United States Patent
Liu (10) Patent No.: US 11,660,060 B2
(45) Date of Patent: May 30, 2023

(54) WHOLE BODY PET AND CT COMBINED DEVICE

(71) Applicant: SHANDONG MADIC TECHNOLOGY CO., LTD., Linyi (CN)

(72) Inventor: Jiguo Liu, Linyi (CN)

(73) Assignee: SHANDONG MADIC TECHNOLOGY CO., LTD., Linyi (CN)

( * ) Notice: Subject to any disclaimer, the term of this patent is extended or adjusted under 35 U.S.C. 154(b) by 92 days.

(21) Appl. No.: 17/264,345

(22) PCT Filed: Apr. 1, 2019

(86) PCT No.: PCT/CN2019/080783
§ 371 (c)(1),
(2) Date: Jan. 29, 2021

(87) PCT Pub. No.: WO2020/042610
PCT Pub. Date: Mar. 5, 2020

(65) Prior Publication Data
US 2021/0298709 A1    Sep. 30, 2021

(30) Foreign Application Priority Data

Aug. 29, 2018  (CN) .......................... 201810993764.3

(51) Int. Cl.
*A61B 6/00*       (2006.01)
*A61B 6/03*       (2006.01)
(Continued)

(52) U.S. Cl.
CPC ............ *A61B 6/5235* (2013.01); *A61B 6/032* (2013.01); *A61B 6/037* (2013.01); *A61B 6/0407* (2013.01);
(Continued)

(58) Field of Classification Search
CPC ....... A61B 6/5235; A61B 6/032; A61B 6/037; A61B 6/0407; A61B 6/06; A61B 6/4035;
(Continued)

(56) References Cited

U.S. PATENT DOCUMENTS

2004/0195512  A1*  10/2004  Crosetto ................ A61B 6/037
                                                      250/363.04
2014/0177794  A1*   6/2014  De Man ............... G01N 23/046
                                                            378/62
(Continued)

FOREIGN PATENT DOCUMENTS

CN      202505368 U    10/2012
CN      103536308 A     1/2014
(Continued)

OTHER PUBLICATIONS

Badawi et al., First Human Imaging Studies with the EXPLORER Total-Body PET Scanner*, Mar. 2019, The Journal of Nuclear Medicine • vol. 60 • No. 3 • pp. 299-303 (Year: 2019).*
(Continued)

*Primary Examiner* — Christine S. Kim
(74) *Attorney, Agent, or Firm* — Scully Scott Murphy & Presser (57) ABSTRACT

A whole body PET and CT combined detector and device, comprising a CT scanner frame (4) and a PET detection chamber (5) at the front and the rear along a common central axis. The CT scanner frame (4) is provided with a housing and also has a cylindrical CT scanning channel vertical to the central axis; the PET detection chamber (5) is formed by a plurality of PET detection modules (6, 7) adjacent to each other, and PET detection crystals (10) are all arranged in a direction towards to the chamber, the PET detection chamber (5) is entirely closed or a first opening is formed at the side adjacent to the CT scanner frame (4); each of the PET detection modules (6, 7) is composed of the PET detection
(Continued)

crystals (10), a photoelectric sensor array (8), and a light guide (9); and except for the first opening, the cross-sectional areas of all gaps of the PET detection chamber (5) are smaller than the detected surface area of the smallest one of the PET detection crystals (10).

9 Claims, 3 Drawing Sheets (51) Int. Cl.
*A61B 6/04* (2006.01)
*A61B 6/06* (2006.01)
*G01T 1/202* (2006.01)

(52) U.S. Cl.
CPC .............. *A61B 6/06* (2013.01); *A61B 6/4035* (2013.01); *A61B 6/4417* (2013.01); *G01T 1/2023* (2013.01)

(58) Field of Classification Search
CPC ... A61B 6/4417; G01T 1/2023; G01T 1/2985; G01T 1/1615
See application file for complete search history.

(56) References Cited

U.S. PATENT DOCUMENTS

| | | | |
|---|---|---|---|
| 2015/0073272 A1 | 3/2015 | Corbeil | |
| 2017/0123084 A1* | 5/2017 | Ferenc | ................. G01T 1/2018 |
| 2018/0184992 A1* | 7/2018 | Li | ........................ A61B 6/5205 |
| 2019/0000406 A1* | 1/2019 | Liu | ........................ G01T 1/2018 |

FOREIGN PATENT DOCUMENTS

| | | | | |
|---|---|---|---|---|
| CN | 103543463 A | | 1/2014 | |
| CN | 105559811 A | | 5/2016 | |
| CN | 107550512 A | | 1/2018 | |
| CN | 107595316 A | | 1/2018 | |
| CN | 113081016 A | * | 7/2021 | ............. A61B 6/037 |
| JP | 2010197140 A | | 9/2010 | |
| JP | 2012088306 A | | 5/2012 | |
| JP | 2017086903 A | | 5/2017 | |

OTHER PUBLICATIONS

Vandenberghe et al., State of the art in total body PET, 2020, pp. 1-33. (Year: 2020).*

Zhang et al., Quantitative image reconstruction for total-body PET imaging using the 2-meter long Explorer scanner, 2017, Phys. Med. Biol. vol. 62, pp. 2465-2485 (Year: 2017).*

International Search Report dated Jul. 1, 2019 received in International Application No. PCT/CN2019/080783.

First Office Action dated Dec. 18, 2019 received in Chinese Patent Application No. CN 201810993764.3 together with an English language translation.

Notice of Reasons for Refusal dated Feb. 1, 2022 received in Japanese Patent Application No. JP 2021-506303 together with an English language translation.

* cited by examiner

- PRIOR ART -

FIG. 1

- PRIOR ART -

WHOLE BODY PET AND CT COMBINED DEVICE

TECHNICAL FIELD

The present disclosure relates to the technical field of PET detectors, and more particularly to a PET detector for detecting the arrangement of crystals and used in parallel and in combination with CT, and a full-angle coincidence PET detector applied to the whole body, none of which was ever seen in the related art.

BACKGROUND

Figure 1:
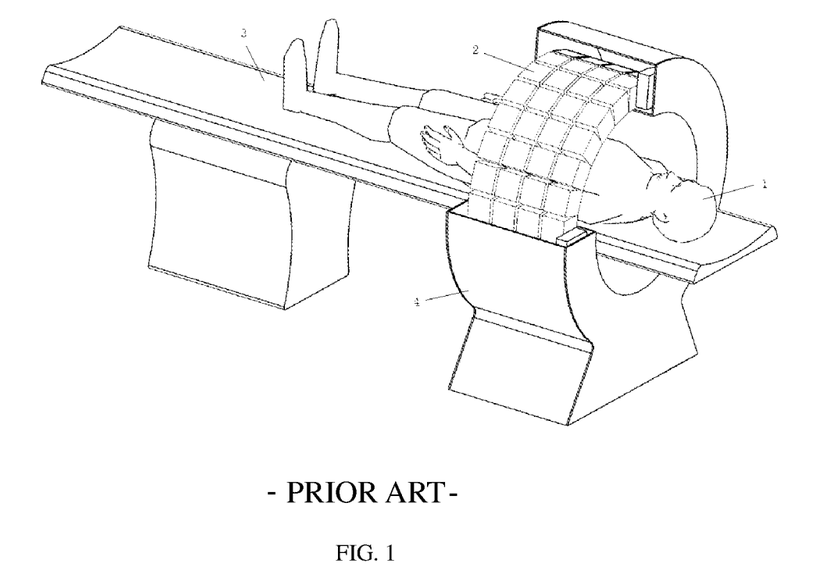
FIG. 1 is a schematic view of a traditional PET detector ring and an object to be detected in the related art.

Positron Emission Tomography (PET) apparatuses are widely used in specificity imaging of animals and human bodies. In PET imaging, it is required to first inject a tracer labeled with a positron nuclide into a scanned object, and then image the distribution of the tracer in the scanned object. The imaging of the position labeled by the tracer has strong specificity, and dynamic imaging may be performed with a high degree of recognition. Traditional PET apparatuses have insufficient axial depth of the detector and can only scan a limited local area at a time. If it is desired to obtain a PET image of the whole body of human, local scanned images of multiple (such as 8-10) beds must be spliced to obtain the image of whole body. There are two problems with this imaging method: first, the imaging speed is slow, each bed takes 1 to 5 minutes for a traditional human body PET apparatus, the axial field of view is about 20 cm, the whole-body imaging requires 8-10 beds and takes at least 8 minutes at a time, and additional calculation time is further required, which may reach 50 minutes for some apparatuses; second, one of the major advantages of PET is that dynamic information of the tracer can be obtained, but it is impossible for the detector with insufficient depth to obtain the dynamic information of the tracer on the whole body, and the images obtained at different beds cannot be spliced to obtain the dynamic information of the whole body; this is an impossible task for the traditional PET apparatus, which is shown in FIG. 1.

Figure 2:
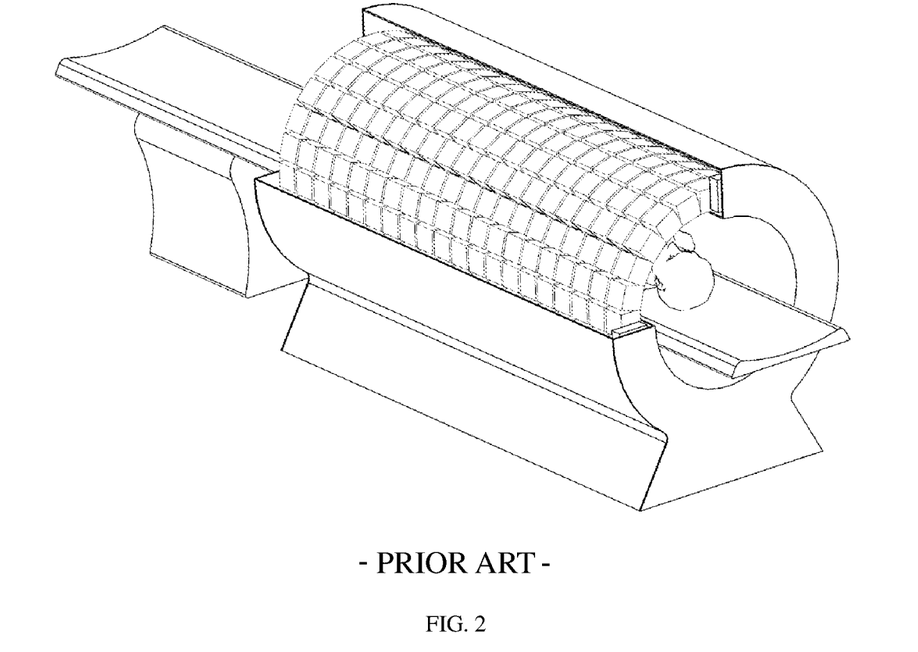
FIG. 2 is a schematic view of an axially lengthened detector ring which has appeared in recent years and an object to be detected.

In special cases, in order to obtain the status of systemic drug metabolism, an axial field of view of extended PET apparatus has appeared in the related art. When the length/depth of the axial field of view exceeds or approaches the length of the scanned object, the whole-body dynamic imaging can be performed on the scanned object. For example, in Sci. Transl. Med, vol. 9, eaaf6169 (2017) 15 Mar. 2017 by Cherry et al., by axially extending the detector ring of the human body PET to 2 meters, dynamic imaging can be performed on the whole human body. However, the size of the PET detector ring of these whole-body imaging apparatuses is completely uniform in the entire axial direction, and the length/depth of the detector is only extended in the axial direction. The problem with such detector ring design is that the sensitivity in the scanning field of view is not uniform enough. The sensitivity is the highest in the middle of the overall detector. As the position moves from a center to both ends of the detector along an axis, the sensitivity drops rapidly, and drops to a very low level at the positions of the two ends of the detector, or even zero. FIG. 2 shows an extended PET apparatus in the related art.

The reason for this phenomenon is that PET adopts a data acquisition method of coincidence detection. When 511 keV gamma rays are simultaneously detected on two exactly opposite detector crystals, this is called a true coincidence event. Only in this situation will the two gamma rays be taken as an effective positron event. Occurrence positions of this positron event are on a straight line between the two crystals, which are positions to be detected. This line is called line of reaction, hereinafter referred to as LOR.

Figure 3:
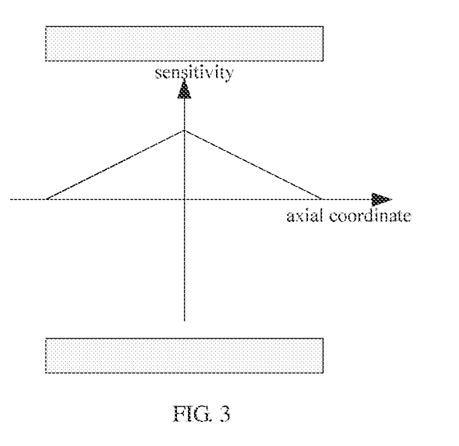
FIG. 3 is a schematic view showing different sensitivities of the axially lengthened detector ring to various internal parts.
Figure 4:
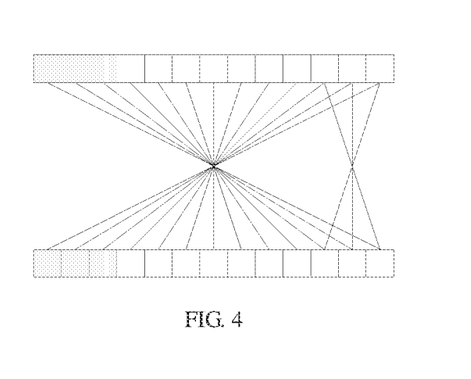
FIG. 4 is a schematic view showing LORs of different detection points captured in the axially lengthened detector ring.

FIG. 4 is a schematic diagram of the LORs of a PET detector in the related art. It can be clearly seen from a comparison between two occurrence positions in the figure that one position is at the center of the axial field of view of the detector, and the other position is not at the center of the axial field of view, but at the edge. Due to the difference in position, the probabilities of detecting LORs occurring from different positions differ greatly. For most LORs that occur from the center, they can be detected as long as they are not horizontal or nearly horizontal; for LORs occurring from the edge, only some LORs that are perpendicular or nearly perpendicular to the axial direction can be detected. The number of LORs that can be detected occurring from non-center positions is significantly lower than the number of LORs occurring from the center, which leads to the fact that the sensitivity becomes lower and lower as the occurrence position deviates from the LOR center. The sensitivity of any point in the PET field of view is determined by a solid angle covered by all LORs passing through the point. The larger the solid angle covered by the LORs is, the greater the sensitivity of the point will be. This relationship between the sensitivity and the position is shown in FIG. 3, which shows that the closer it is to the center of gravity, the higher the sensitivity will be; on the contrary, the sensitivity at the edge is very low.

This leads to, for example, that the sensitivities of the positions of the human head and feet are much lower than that of the abdomen in the center of the field of view during the whole-body PET scanning. This problem cannot be solved by simply extending the axial length of the detector. Specifically, even if the length of the detector ring is 2 meters, when observing the dynamic image of the whole body, only the dynamic image near the abdomen meets the observation requirements, and the dynamic images near the head and feet are still of no confidence and cannot be applied. It still needs 2-3 times of splicing to obtain a better whole-body image. The detector ring is greatly lengthened and the cost of the instrument is greatly increased. However, it can be seen from the above analysis that a whole-body image or a whole-body dynamic image cannot be well obtained at a time. The closer it is to the head and feet, the lower the confidence of the obtained image data will be, and the problem of one-time whole-body imaging or one-time dynamic imaging is not fundamentally solved.

On the other hand, as compared with traditional technologies such as CT, the emergence of PET effectively compensates the weaknesses of traditional technologies such as CT. Recently, there are many technologies that combine PET with CT to complement each other with complementary advantages.

The rapid development of PET-CT technology has not only made the field of nuclear medicine full of vitality, but also has caused great interest in the field of radiology. With PET-CT, nuclear medicine doctors will be more accurate in their positioning of metabolic changes, and radiologists will be more accurate in characterization of morphological and structural changes. Therefore, PET-CT has received rapid development in just a few years and is constantly updating. Although PET-CT was officially commercialized at the end of 2000, its sales share accounted for 65% of the total PET by 2003, and this value increased to 95% in 2004.

At present, there are mainly three manufacturers offering commercial PET-CT: the Biograph and Reveal series coproduced by Siemens and CTI, which, while presenting a good quality, still adopts the design concept of serial connection of detectors of a CT ring and a PET ring, and which has an effect similar to that of superimposition of two instruments; the Discovery LS and Discovery ST series provided by GE, wherein in this series of product, PET and CT are mainly combined together or installed in a single housing, the apparatus has a small volume, but PET and CT have a large mutual electromagnetic influence, and generally they are not working at the same time; and Gemini type PET-CT provided by Philips, which has a split design of CT and PET with a gap in the middle, and the rear part can be moved by a certain distance as needed. This open design effectively reduces the patient's claustrophobia in the channel and facilitates some operations close to the patient during the examination, such as biopsy under CT guidance. The diameter of the CT is 70 cm, and the diameter of the PET is 63 cm.

It can be seen that in all the existing PET-CT designs, the convenience degree of combined use is improved and the space is saved by improving the setting of PET and CT respectively and improving the coordination and cooperation between the two. Neither of them has provided a PET device for one-time scanning of the whole body for existing CT devices. The image information generated by such a combination still is images of a ring CT and a ring PET. The whole-body image cannot be given at a time, and the sensitivity of LOR captured by the image is insufficient. It is even not possible to give a dynamic image of the whole body at a time. The result of PET-CT obtained by this simple splicing has only common mutual reference value and cannot give strong guidance information.

SUMMARY

A first object of the present disclosure is to solve the problem in the related art that the CT-PET is only a simple superimposition of common ring CT and ring PET, and it cannot generate a whole-body image and a whole-body dynamic image at a time, but can only generate comparison information of a common CT image of a certain part such as head and chest and a PET image with insufficient sensitivity, which has insufficient reference value; in view of this situation of lacking an effective solution, the present disclosure provides a perfect PET-CT detector solution, by means of which a credible high-sensitivity whole-body image is obtained at a time, and a CT image can also be given in a targeted manner. This way of solving the problem has not yet appeared in the related art, and the problem of sensitivity defect of PET or PET-CT existing in the related art is even not explicitly proposed in the related art. In the related art, it is believed that the PET detection cavity can be extended to obtain a whole-body image, but it has not been thought that such a whole-body image is still unusable and cannot meet the requirements. In this way, if the whole-body PET image group is obtained first, then a clear and strongly targeted guidance can be provided for the subsequent CT scanning in terms of scanning part and scanning mode.

A whole-body PET and CT combined detector is provided, which includes: a CT scanning frame and a PET detection cavity which are arranged at the front and rear respectively along a common central axis; wherein the CT scanning frame has a housing and has a cylindrical CT scanning channel perpendicular to the central axis; the PET detection cavity is formed by a plurality of PET detection modules arranged adjacent to each other, and PET detection crystals are all arranged in a direction toward an interior of the cavity; the PET detection cavity is entirely closed, or is formed with a first opening on a side adjacent to the CT scanning frame; each of the plurality of PET detection modules is composed of the PET detection crystals, a photosensor array and a light guide; except for the first opening, the cross-sectional areas of all gaps of the PET detection cavity are each smaller than a detection surface area of the smallest one of the PET detection crystals.

The CT scanning frame further includes, but is not limited to, the following devices: an X-ray tube, a filter (Bucky), a collimator, a reference detector, and a detector.

When the PET detection cavity is entirely closed, the PET detection cavity is in a first form or a second form or a third form or a fourth form; an end of the PET detection cavity that is perpendicular to the central axis has a first end cap allowing for entry and exit of an entire human body module, and the first end cap is equipped with a mechanical structure that can be opened and completely closed with respect to the PET detection cavity; wherein 1) in the first form, the PET detection cavity has a cylindrical shape, and is composed of a barrel in the middle and two planar end caps at both ends; the barrel is composed of a plurality of detection module rings closely arranged to form a cylindrical shape, and each of the detection module rings is composed of a certain number of detection modules arranged circumferentially into a ring shape in a crystal-inward manner; the planar end cap is composed of a certain number of detection modules arranged in parallel into a disc shape or an approximate disc shape with detection surfaces of the crystals facing inward, and an inner side surface of the planar end cap formed into an approximately circular shape has a size larger than a circular opening of the barrel; the first end cap in the first form is one of the two planar end caps; 2) in the second form, the PET detection cavity has a capsule shape, and is composed of a barrel in the middle and two concave curved end caps at both ends; the barrel is composed of a plurality of detection module rings closely arranged to form a cylindrical shape, and each of the detection module rings is composed of a certain number of detection modules arranged circumferentially into a ring shape with detection surfaces of the crystals facing inward; the concave curved end cap is composed of a certain number of detection modules arranged in a certain curvature with detection surfaces of the crystals concave inward, and the cross section of the concave curved end cap perpendicular to an axis of the barrel is larger than a circular opening of the barrel; the concave curved end cap is specifically one of the following three situations: a hemispherical end cap, a less-than-half ellipsoidal end cap or a less-than-half spherical crown-shaped end cap; the first end cap in the first form is one of the two concave curved end caps; 3) in the third form, the PET detection cavity has an ellipsoidal shape with a>b=c, and is composed of two upper and lower hemi-ellipsoids or two left and right hemi-ellipsoids, or is composed of two left and right hemi-ellipsoids with a barrel sandwiched therebetween; the upper and lower hemi-ellipsoids are mirror-symmetrical, and the left and right hemi-ellipsoids are mirror-symmetrical; the barrel is composed of a plurality of detection module rings closely arranged to form a cylindrical shape or a shape of truncated ellipsoid in the middle, which satisfies a>b=c; each of the detection module rings in the barrel is composed of a certain number of detection modules arranged circumferentially into a ring shape with detection surfaces of the crystals facing inward; the first end cap in the third form is located on an end of the detection cavity perpendicular to the central axis, and has a shape truncated from the a-axis end of a>b=c; and 4) in the fourth form, the PET detection cavity has a regular polygonal prism shape and is composed of a barrel in the middle and two planar end caps at both ends; the barrel is composed of a plurality of detection module rings closely arranged to form a regular polygonal prism shape, and each of the detection module rings is composed of a certain number of detection modules arranged circumferentially into a regular polygon shape with detection surfaces of the crystals facing inward; the planar end cap is composed of a certain number of detection modules arranged in parallel into a disc shape or an approximate disc shape or a regular polygon shape or an approximately regular polygon shape with detection surfaces of the crystals facing inward; an inner side surface of the planar end cap formed into an approximately circular shape has a size larger than a regular polygon opening of the barrel; the first end cap in the fourth form is one of the two planar end caps.

When the PET detection cavity is formed with the first opening on the side adjacent to the CT scanning frame, the PET detection cavity is in the first form or the second form or the third form or the fourth form with the first end cap removed.

A coincidence circuit is connected between every two PET detection modules; each of the PET detection modules has the following specific structure: the detector housing, the photosensor array, the light guide, and the PET detection crystals are disposed in order from the outside to the inside; the light guide is tightly coupled with both the photosensor array and the PET detection crystals; the material of the PET detection crystals is a scintillation crystal, and the scintillation crystal is composed of one or more crystal blocks; in the fourth form, the regular polygonal prism is a regular hexagonal prism or a regular octagonal prism, and the regular polygon is a regular hexagon or a regular octagon.

The surfaces of the PET detection crystals that face inward are all planar or approximately planar; the crystal block is specifically a crystal strip array composed of a plurality of crystal strips, or is composed of one or more integrally cut crystals; the material of the scintillation crystal is selected from one or more of bismuth germanate (BGO) crystals, sodium iodide (NaI) crystals, NaI(Tl) single crystals, lutetium silicate (LSO) crystals, gadolinium silicate (GSO) crystals and yttrium lutetium silicate (LYSO).

Spacers made of high atomic number substance are installed between all the detection module rings, or spacers made of high atomic number substance are installed between some of the detection module rings, or no spacers are installed between all the detection module rings.

The high atomic number substance is lead or tungsten.

The present disclosure also provides a whole-body PET and CT combined detector apparatus, which includes the whole-body PET and CT combined detector as described above, wherein the whole-body PET and CT combined detector apparatus further includes a power supply circuit, a communication line, a PC terminal, a PET bearing bracket, a CT bearing bracket, a scanning bed, a bed frame, an electric guide rail between the scanning bed and the bed frame, a PET working power source, a CT working power source, and a console terminal.

The PET bearing bracket fixes and supports all of the plurality of PET detection modules on the PET detection cavity, and the PET bearing bracket can drive the detection cavity to rotate at an arbitrary angle, and can also drive the detection cavity to translate in any direction.

The mechanical structure that can be opened and completely closed with respect to the PET detection cavity is a hinge structure that can be automatically or manually opened and closed in cooperation with the first end cap, or a rotation mechanism that enables the first end cap to be rotationally opened and closed while maintaining perpendicular to the central axis, or a translation mechanism that enables the first end cap to be opened and closed by translating while maintaining perpendicular to the central axis.

The PC terminal has a PET signal acquisition and operation analysis system, and a CT signal acquisition and operation analysis system.

The power supply circuit is connected to the PET working power source and the CT working power source; the PET working power source and the CT working power source provide electrical energy at a rated voltage to the communication line, the PC terminal, the PET bearing bracket, the CT bearing bracket, the scanning bed, the bed frame, the electric guide rail between the scanning bed and the bed frame, the console terminal and all the PET detection modules.

Signals detected by all the PET detection modules are transmitted to the PET signal acquisition and operation analysis system through the communication line, and signals received by the detector and the reference detector in the CT scanning frame are transmitted to the CT signal acquisition and operation analysis system through the communication line.

The scanning bed is placed horizontally on the bed frame, a guide rail is provided between the scanning bed and the bed frame, and the scanning bed can move back and forth along the guide rail in a direction parallel to the central axis.

A lower portion of the PET detection cavity has a gap through which one or more bed frames can pass; and in the case where the PET detection cavity is provided with the first opening and the first end cap, the bed frame and the electric guide rail both have interrupted front and rear ends formed at the first opening, and such interruption enables the first end cap to be opened and closed without being hindered.

A plurality of vertical pillars are provided under the bed frame along the central axis, and a horizontal, height-adjustable and stably supported pillar base is provided under each pillar, the guide rail is an integral rail, or is a pair of guide rails on both sides of the central axis.

A whole-body PET and CT combined detection method is implemented by using the whole-body PET and CT combined detector apparatus according to claim 7, wherein the method includes: 1) a CT scanning step: placing an object to be detected onto the scanning bed, moving the scanning bed inwardly until a pre-scanning part is located in a middle position of the cylindrical CT scanning channel, and performing CT scanning detection to obtain a plurality of CT scanned static images; 2) a PET detecting step: for the case where the PET detection cavity has the first opening, continuing to move the object to be detected inwardly under the driving of the scanning bed until the object to be detected completely enters the PET detection cavity; or for the case where the PET detection cavity is entirely closed, opening the first end cap, continuing to move the object to be detected inwardly under the driving of the scanning bed until the object to be detected completely enters the PET detection cavity, and completely closing the first end cap; performing PET scanning detection on the object to be detected to obtain a plurality of PET scanned static images and at least one dynamic image; and determining one or more parts of interest according to the plurality of PET scanned static images and the at least one dynamic image; 3) a CT re-scanning step: selecting one re-scanning part from the one or more parts of interest, moving the scanning bed outward with the object to be detected carried thereon until the scanning part is located in the middle position of the cylindrical CT scanning channel, and then performing CT scanning detection again to obtain a plurality of CT scanned static images.

The object to be detected is a human body detection module or a human body.

A whole-body PET and CT combined detection method is implemented by using the whole-body PET and CT combined detector apparatus according to claim 7, wherein the method includes: 1) a PET detecting step: for the case where the PET detection cavity has the first opening, continuing to move the object to be detected inwardly under the driving of the scanning bed until the object to be detected completely enters the PET detection cavity; or for the case where the PET detection cavity is entirely closed, opening the first end cap, continuing to move the object to be detected inwardly under the driving of the scanning bed until the object to be detected completely enters the PET detection cavity, and completely closing the first end cap; performing PET scanning detection on the object to be detected to obtain a plurality of PET scanned static images and at least one dynamic image; and determining one or more parts of interest according to the plurality of PET scanned static images and the at least one dynamic image; and 2) a CT scanning step: selecting one part of interest from the one or more parts of interest, moving the scanning bed outward with the object to be detected carried thereon until the part of interest is located in the middle position of the cylindrical CT scanning channel, and performing CT scanning detection to obtain a plurality of CT scanned static images.

The present disclosure has the following two main advantages. First, it completely solves the problem of one-time acquisition of a whole-body image and a whole-body dynamic image. With the detector of the present disclosure, almost all LORs of the true coincidence events can be captured instantly. It fundamentally ensures the success rate of one-time imaging. Second, it completely solves the sensitivity problem of occurrence event capture. For example, only from the perspective of lengthening the detector, if it is desired to capture the occurrence positions on a more than 1-meter long human body with high sensitivity, the length of the detector may need to be 4 meters long to enable the sensitivity of the whole-body capture to meet the requirements. This is very uneconomical, since crystals such as bismuth germanate are expensive. The method of the present disclosure requires less materials than a 4-meter-long detector ring, but achieves a better effect. The sensitivities of nearly all occurrence positions are almost the same. This is something that no one has thought of and no one can achieve in the related art. Third, the value of images obtained by PET-CT is improved to a higher level. On one hand, not only the PET images obtained simultaneously with CT are systemic, but also the whole-body dynamic images can be obtained due to the extremely high sensitivity and the extremely high resolution. Therefore, the reference value is multiplied. For example, the whole-body PET detection can be performed first, and after the strong directivity information is obtained, the precise CT detection is performed on the part of interest, so that the image information obtained at a time has strong directivity. As compared with the general PET-CT combined "blind detection", the practical value is immense.

BRIEF DESCRIPTION OF THE DRAWINGS

The accompanying drawings required to be used in the description of the embodiments of the present disclosure or the related art are described briefly below, so that the technical solutions according to the embodiments of the present disclosure or according to the related art will become clearer. It is apparent that the accompanying drawings in the following description show only some embodiments of the present disclosure. For those skilled in the art, other accompanying drawings may also be obtained according to these drawings provided, without any creative work.

Reference signs: 1. scanning bed; 2. electric guide rail; 3. bed frame; 4. CT scanning frame; 5. PET detection cavity; 6. PET detection module; 7. PET detection module; 8. photosensor array; 9. light guide; 10. PET detection crystal.

DETAILED DESCRIPTION

Preferred embodiments of the present disclosure will be described in detail below with reference to the accompanying drawings, so that the advantages and features of the present disclosure can be more easily understood by those skilled in the art, thereby making a clearer and definite definition of the scope of protection of the present disclosure.

Specific Embodiments

First Embodiment

A whole-body PET and CT combined detector is provided, which includes: a CT scanning frame and a PET detection cavity which are arranged at the front and rear respectively along a common central axis; wherein the CT scanning frame has a housing and has a cylindrical CT scanning channel perpendicular to the central axis; the PET detection cavity is formed by a plurality of PET detection modules arranged adjacent to each other, and PET detection crystals are all arranged in a direction toward an interior of the cavity; the PET detection cavity is entirely closed, or is formed with a first opening on a side adjacent to the CT scanning frame; each of the plurality of PET detection modules is composed of the PET detection crystals, a photosensor array and a light guide; except for the first opening, the cross-sectional areas of all gaps of the PET detection cavity are each smaller than a detection surface area of the smallest one of the PET detection crystals. The core inventive idea of the present application is included herein, that is, the CT scanning frame and the whole-body PET detection cavity are arranged in order, and a simple and direct combined use of whole-body PET and CT can be realized as long as the two cavities herein are arranged side by side in order, so that one scanning bed can drive the object to be detected to move between the two easily, and the advantages of the two can directly complement each other.

The CT scanning frame further includes, but is not limited to, the following devices: an X-ray tube, a filter (Bucky), a collimator, a reference detector, and a detector. The CT scanning frame mentioned herein is the most common CT scanning frame, but structures and components of other similarly configured CT scanning frames or other CT scanning frames with similar functions are also applicable herein.

When the PET detection cavity is entirely closed, the PET detection cavity is in a first form or a second form or a third form or a fourth form; an end of the PET detection cavity that is perpendicular to the central axis has a first end cap allowing for entry and exit of an entire human body module, and the first end cap is equipped with a mechanical structure that can be opened and completely closed with respect to the PET detection cavity; wherein 1) in the first form, the PET detection cavity has a cylindrical shape, and is composed of a barrel in the middle and two planar end caps at both ends; the barrel is composed of a plurality of detection module rings closely arranged to form a cylindrical shape, and each of the detection module rings is composed of a certain number of detection modules arranged circumferentially into a ring shape in a crystal-inward manner, the planar end cap is composed of a certain number of detection modules arranged in parallel into a disc shape or an approximate disc shape with detection surfaces of the crystals facing inward, and an inner side surface of the planar end cap formed into an approximately circular shape has a size larger than a circular opening of the barrel; the first end cap in the first form is one of the two planar end caps; 2) in the second form, the PET detection cavity has a capsule shape, and is composed of a barrel in the middle and two concave curved end caps at both ends; the barrel is composed of a plurality of detection module rings closely arranged to form a cylindrical shape, and each of the detection module rings is composed of a certain number of detection modules arranged circumferentially into a ring shape with detection surfaces of the crystals facing inward; the concave curved end cap is composed of a certain number of detection modules arranged in a certain curvature with detection surfaces of the crystals concave inward, and the cross section of the concave curved end cap perpendicular to an axis of the barrel is larger than a circular opening of the barrel; the concave curved end cap is specifically one of the following three situations: a hemispherical end cap, a less-than-half ellipsoidal end cap or a less-than-half spherical crown-shaped end cap; the first end cap in the first form is one of the two concave curved end caps; 3) in the third form, the PET detection cavity has an ellipsoidal shape with $a>b=c$, and is composed of two upper and lower hemi-ellipsoids or two left and right hemi-ellipsoids, or is composed of two left and right hemi-ellipsoids with a barrel sandwiched therebetween; the upper and lower hemi-ellipsoids are mirror-symmetrical, and the left and right hemi-ellipsoids are mirror-symmetrical; the barrel is composed of a plurality of detection module rings closely arranged to form a cylindrical shape or a shape of truncated ellipsoid in the middle, which satisfies $a>b=c$; each of the detection module rings in the barrel is composed of a certain number of detection modules arranged circumferentially into a ring shape with detection surfaces of the crystals facing inward; the first end cap in the third form is located on an end of the detection cavity perpendicular to the central axis, and has a shape truncated from the a-axis end of $a>b=c$; and 4) in the fourth form, the PET detection cavity has a regular polygonal prism shape and is composed of a barrel in the middle and two planar end caps at both ends; the barrel is composed of a plurality of detection module rings closely arranged to form a regular polygonal prism shape, and each of the detection module rings is composed of a certain number of detection modules arranged circumferentially into a regular polygon shape with detection surfaces of the crystals facing inward; the planar end cap is composed of a certain number of detection modules arranged in parallel into a disc shape or an approximate disc shape or a regular polygon shape or an approximately regular polygon shape with detection surfaces of the crystals facing inward; an inner side surface of the planar end cap formed into an approximately circular shape has a size larger than a regular polygon opening of the barrel; the first end cap in the fourth form is one of the two planar end caps. The above four forms are not exhaustive. In fact, similar shapes of the above four forms which can be used for whole-body covered detection of human subjects without too much waste can be trial-produced and can be operated by the applicant. Described above are only several simple ways of producing and designing.

When the PET detection cavity is formed with the first opening on the side adjacent to the CT scanning frame, the PET detection cavity is in the first form or the second form or the third form or the fourth form with the first end cap removed.

A coincidence circuit is connected between every two PET detection modules; each of the PET detection modules has the following specific structure: the detector housing, the photosensor array, the light guide, and the PET detection crystals are disposed in order from the outside to the inside; the light guide is tightly coupled with both the photosensor array and the PET detection crystals; the material of the PET detection crystals is a scintillation crystal, and the scintillation crystal is composed of one or more crystal blocks; in the fourth form, the regular polygonal prism is a regular hexagonal prism or a regular octagonal prism, and the regular polygon is a regular hexagon or a regular octagon. The above design of the photosensor array, the light guide and the PET detection crystals, when combined with the whole-body covered detection cavity, enables almost all LOR events to be captured, thus having an extremely high detection sensitivity.

The surfaces of the PET detection crystals that face inward are all planar or approximately planar; the crystal block is specifically a crystal strip array composed of a plurality of crystal strips, or is composed of one or more integrally cut crystals; the material of the scintillation crystal is selected from one or more of bismuth germanate (BGO) crystals, sodium iodide (NaI) crystals, NaI(Tl) single crystals, lutetium silicate (LSO) crystals, gadolinium silicate (GSO) crystals and yttrium lutetium silicate (LYSO). In addition to the above ones, other commercially available detection crystals suitable for positron capture are also adapted to be used in the technical solutions of the present application.

Spacers made of high atomic number substance are installed between all the detection module rings, or spacers made of high atomic number substance are installed between some of the detection module rings, or no spacers are installed between all the detection module rings. The high atomic number substance is lead or tungsten.

Second Embodiment

A whole-body PET and CT combined detector apparatus is provided, which includes the whole-body PET and CT combined detector as described above, wherein the whole-body PET and CT combined detector apparatus further includes a power supply circuit, a communication line, a PC terminal, a PET bearing bracket, a CT bearing bracket, a scanning bed, a bed frame, an electric guide rail between the scanning bed and the bed frame, a PET working power source, a CT working power source, and a console terminal.

The PET bearing bracket fixes and supports all of the plurality of PET detection modules on the PET detection cavity, and the PET bearing bracket can drive the detection cavity to rotate at an arbitrary angle, and can also drive the detection cavity to translate in any direction. The fixing and moving functions of the PET bearing bracket herein enable the detection cavity to move upward, downward, leftward and rightward, to rotate, and to perform various position adjustments to meet the adjustment needs under various coordination with other devices. It can meet the detection needs in various complicated situations.

The mechanical structure that can be opened and completely closed with respect to the PET detection cavity is a hinge structure that can be automatically or manually opened and closed in cooperation with the first end cap, or a rotation mechanism that enables the first end cap to be rotationally opened and closed while maintaining perpendicular to the central axis, or a translation mechanism that enables the first end cap to be opened and closed by translating while maintaining perpendicular to the central axis. The hinge structure that can be automatically or manually opened and closed in cooperation with the first end cap may be similar to the opening and closing of the general drum washing machine; the rotation mechanism that enables the first end cap to be rotationally opened and closed while maintaining perpendicular to the central axis implements the opening and closing by rotating in a plane perpendicular to the central axis, which requires designing a suitable rubber sealing fitting on the first end cap and the detection cavity to facilitate sealing; the translation mechanism that enables the first end cap to be opened and closed by translating while maintaining perpendicular to the central axis specifically may be sliding grooves at least on two sides, which are designed on the detection cavity so that the first end cap can slide in and out.

The PC terminal has a PET signal acquisition and operation analysis system, and a CT signal acquisition and operation analysis system; both systems are capable of receiving CT and PET scanning signals according to preset adjustment values, and converting them into a plurality of images or a video stream according to a time sequence.

The power supply circuit is connected to the PET working power source and the CT working power source; the PET working power source and the CT working power source provide electrical energy at a rated voltage to the communication line, the PC terminal, the PET bearing bracket, the CT bearing bracket, the scanning bed, the bed frame, the electric guide rail between the scanning bed and the bed frame, the console terminal and all the PET detection modules.

Signals detected by all the PET detection modules are transmitted to the PET signal acquisition and operation analysis system through the communication line, and signals received by the detector and the reference detector in the CT scanning frame are transmitted to the CT signal acquisition and operation analysis system through the communication line. The communication line is, for example, a serial bus, an IDE line, or a data fiber.

The scanning bed is placed horizontally on the bed frame, a guide rail is provided between the scanning bed and the bed frame, and the scanning bed can move back and forth along the guide rail in a direction parallel to the central axis. When the PET detection cavity needs to be completely closed, that is, when the first opening is provided and the guide rail and the bed frame may be set to have two ends, for example, there is an interruption of 30-60 cm in the middle. Such a design not only takes into consideration the complete closure of the PET detection cavity, but also will not cause derailing or falling of the scanning bed when it continues to move inward, and the scanning bed will engage with the guide rail in front of the interruption before falling.

A lower portion of the PET detection cavity has a gap through which one or more bed frames can pass; and in the case where the PET detection cavity is provided with the first opening and the first end cap, the bed frame and the electric guide rail both have interrupted front and rear ends formed at the first opening, and such interruption enables the first end cap to be opened and closed without being hindered. For example, in the lower portion of the PET detection cavity, there is a gap through which three bed frames can pass. For example, there are five bed frames on the outer side of the PET detection cavity to support the entire guide rail.

A plurality of vertical pillars are provided under the bed frame along the central axis, and a horizontal, height-adjustable and stably supported pillar base is provided under each pillar, the guide rail is an integral rail, or is a pair of guide rails on both sides of the central axis.

Third Embodiment

Figure 5:
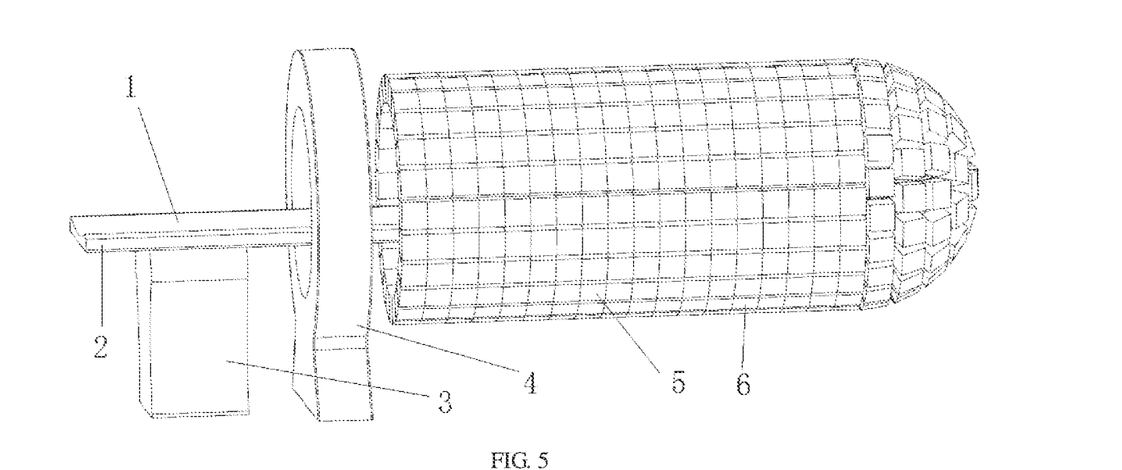
FIG. 5 is a schematic view of a PET detection cavity having a first opening in the PET-CT, wherein the PET detection cavity is composed of a cylindrical barrel in the middle and a hemispherical closed end portion on the outer side, and the inner side is opened to form the first opening.
Figure 6:
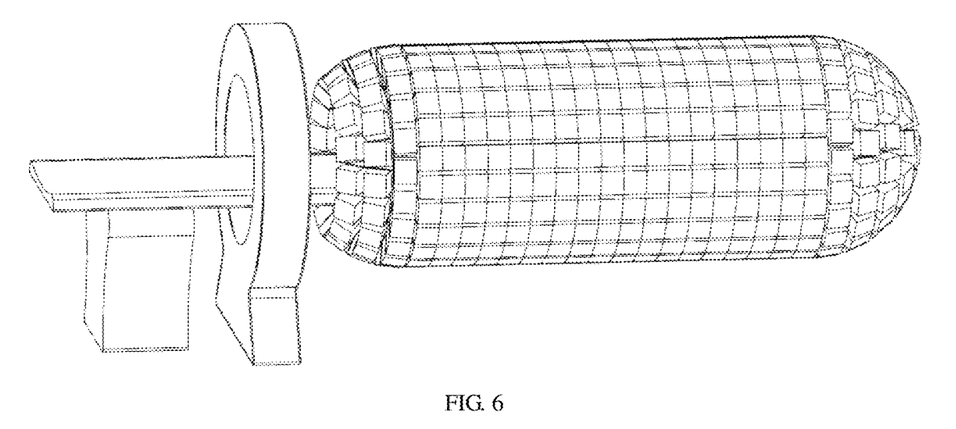
FIG. 6 is a schematic view of a PET detection cavity having a first opening in the PET-CT, wherein the PET detection cavity is composed of a cylindrical barrel in the middle and a first opening defined by an approximately ¼ sphere on the inner side, and the outer side is closed by a hemispherical end portion.
Figure 7:
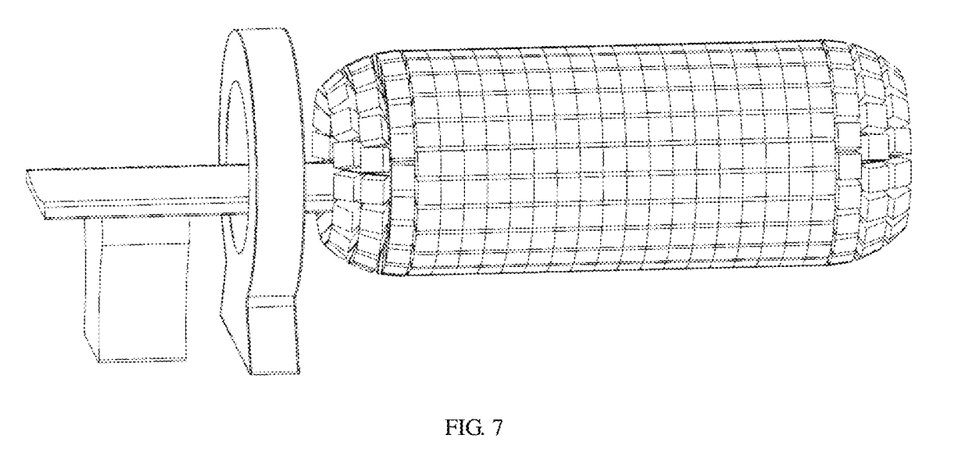
FIG. 7 is a schematic view of a PET detection cavity having a first opening, and a second opening on the outer side in the PET-CT, wherein the first opening is defined by an approximately ¼ sphere on the inner side, and the second opening is defined by an approximately ¼ sphere on the outer side.
Figure 8:
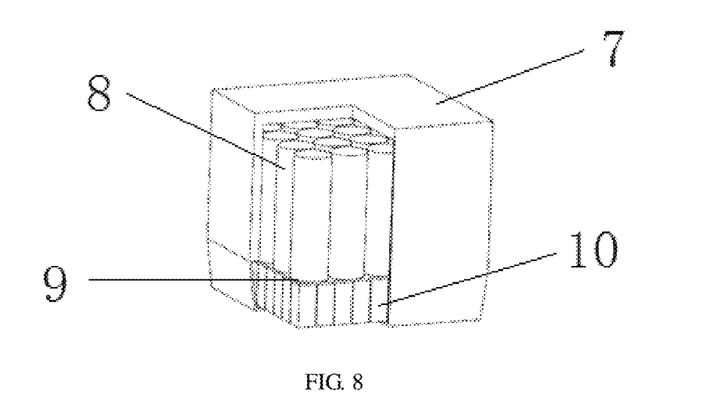
FIG. 8 is a schematic view of a PET detection module with a housing partially cut away.

As shown in FIG. 5, the height of the scanning bed is set such that the center line of the human body module lying thereon coincides with the central axis of the apparatus. When the scanning bed 1 moves back and forth, the center line of the human body module substantially coincides with the central axis, or the offset is small. The movability of the electric guide rail 2 enables the scanning bed 1 to move back and forth. The guide rail 2 is a whole piece, and the center line of the guide rail 2 is parallel to the central axis and is located slightly below the central axis, so that the center line of the human body or the human body module coincides with the central axis. Lower ends on both sides of the scanning bed 1 have inwardly buckled sliding portions which are just snap-fitted on both sides of the guide rail 2 so that the scanning bed is located on both sides of the central axis to ensure the level of the scanning bed during moving. Only one bed frame is shown in FIG. 5, but in real situations, at least six bed frames have to be provided, such as one bed frame on the outer side of the CT scanning frame, one bed frame on the inner side of the CT scanning frame, two bed frames at two ends at the interruption of the guide rail to maintain the level, and at least two bed frames inserted into the interior of the PET detection cavity through the gap from the lower portion of the PET detection cavity. The gap herein only serves for insertion of the bed frame, so it will have no substantive effect on the detection sensitivity.

Fourth Embodiment

A whole-body PET and CT combined detection method is implemented by using the whole-body PET and CT combined detector apparatus according to claim 7, wherein the method includes: 1) a CT scanning step: placing an object to be detected onto the scanning bed, moving the scanning bed inwardly until a pre-scanning part is located in a middle position of the cylindrical CT scanning channel, and performing CT scanning detection to obtain a plurality of CT scanned static images; 2) a PET detecting step: for the case where the PET detection cavity has the first opening, continuing to move the object to be detected inwardly under the driving of the scanning bed until the object to be detected completely enters the PET detection cavity; or for the case where the PET detection cavity is entirely closed, opening the first end cap, continuing to move the object to be detected inwardly under the driving of the scanning bed until the object to be detected completely enters the PET detection cavity, and completely closing the first end cap; performing PET scanning detection on the object to be detected to obtain a plurality of PET scanned static images and at least one dynamic image; and determining one or more parts of interest according to the plurality of PET scanned static images and the at least one dynamic image; 3) a CT re-scanning step: selecting one re-scanning part from the one or more parts of interest, moving the scanning bed outward with the object to be detected carried thereon until the scanning part is located in the middle position of the cylindrical CT scanning channel, and then performing CT scanning detection again to obtain a plurality of CT scanned static images. The object to be detected is a human body detection module or a human body.

In this way, PET-CT detection can be used to effectively correct CT results, or to effectively change the way of CT detection. Due to the characteristics of CT scanning, it has insufficient understanding of the intuitiveness, integrity and accuracy of the detection results, and requires very high-order graph reading experience. With the assistance of PET results, the CT results can be effectively corrected, or better CT results can be obtained.

Fifth Embodiment

A whole-body PET and CT combined detection method is implemented by using the whole-body PET and CT combined detector apparatus according to claim 7, wherein the method includes: 1) a PET detecting step: for the case where the PET detection cavity has the first opening, continuing to move the object to be detected inwardly under the driving of the scanning bed until the object to be detected completely enters the PET detection cavity; or for the case where the PET detection cavity is entirely closed, opening the first end cap, continuing to move the object to be detected inwardly under the driving of the scanning bed until the object to be detected completely enters the PET detection cavity, and completely closing the first end cap; performing PET scanning detection on the object to be detected to obtain a plurality of PET scanned static images and at least one dynamic image; and determining one or more parts of interest according to the plurality of PET scanned static images and the at least one dynamic image; and 2) a CT scanning step: selecting one part of interest from the one or more parts of interest, moving the scanning bed outward with the object to be detected carried thereon until the part of interest is located in the middle position of the cylindrical CT scanning channel, and performing CT scanning detection to obtain a plurality of CT scanned static images.

The PET-CT combined detection has a further advantage that, for example, in general physical examination, if the possible lesion location is completely unknown, monitoring by whole-body PET can directly and clearly find where the lesion is, without segmented estimation scanning by CT. In the case of whole-body PET-CT combined use, the whole-body PET scanning is performed first, so that the lesion can be found in the shortest time, and it is determined which part is further targeted at, and in which manner the CT scanning is performed, so as to improve the detection efficiency and the targeting to a certain degree.

Described above are only specific embodiments of the present disclosure, but the scope of protection of the present disclosure is not limited to this. Any change or replacement that can be contemplated without creative work should be covered within the scope of protection of the present disclosure. Therefore, the scope of protection of the present disclosure shall be accorded with the scope of the claims.

Sixth Embodiment

A coincidence circuit is connected between every two PET detection modules; each of the PET detection modules has the following specific structure: a detector housing is wrapped on the outside, a photoelectric sensor array is disposed outwardly, and a PET detection crystal is disposed inwardly. A light guide is disposed between the photoelectric sensor array and the PET detection crystal. The light guide is tightly coupled with both the photoelectric sensor array and the PET detection crystal; the PET detection crystal is a scintillation crystal.

The coincidence circuit is necessary for calculating the LOR, and can filter out the LORs of the true coincidence events most quickly. A portion of the detector housing that is located outside the PET detection crystal is designed as an opening, or the material used does not affect the collection of the positron emission signal.

The scintillation crystal is composed of a crystal strip array, and the crystal strip array is composed of a plurality of crystal strips; or the scintillation crystal is composed of one or more crystal blocks, each of which is composed of one or more integrally cut crystals. Two processing settings are proposed above, in which the crystal block method is simple in processing, and the crystal strip array method has a good coupling effect with the light guide and a faster response speed.

The material of the scintillation crystal is selected from one or more of bismuth germanate (BGO) crystals, sodium iodide (NaI) crystals, NaI(Tl) single crystals, lutetium silicate (LSO) crystals, gadolinium silicate (GSO) crystals and yttrium lutetium silicate (LYSO). After experimentation, all existing scintillation crystals can be used for the PET detection in the present application, and the actually available scintillation crystals are not limited to the crystal types actually listed above. Other available scintillation crystals can be used as the PET detection crystals in the present application.

Spacers made of high atomic number substance are installed between all the detection module rings, or spacers made of high atomic number substance are installed between some of the detection module rings, or no spacers are installed between all the detection module rings; the high atomic number substance is lead or tungsten. Herein, the present technical solution can also be implemented even if no spacer is installed at all. However, installing the spacer can appropriately reduce the crosstalk and the electromagnetic influence between the PET detection modules, which is a way that may be considered. Herein, the spacers may be all installed, or may be installed between some modules according to specific conditions and needs, but not installed in other positions, all of which are possible.

Described above are only specific embodiments of the present disclosure, but the scope of protection of the present disclosure is not limited to this. Any change or replacement that can be contemplated without creative work should be covered within the scope of protection of the present disclosure. Therefore, the scope of protection of the present disclosure shall be accorded with the scope of the claims.

The invention claimed is:

1. A whole-body PET and CT combined detector, comprising:
    a CT scanning frame and a PET detection cavity, wherein the CT scanning frame and the PET detection cavity are arranged at a front end and a rear end, respectively, along a common central axis;
    wherein:
    the CT scanning frame has a housing and has a cylindrical CT scanning channel perpendicular to the central axis;
    the PET detection cavity is formed by a plurality of PET detection modules arranged adjacent to each other; the PET detection cavity is entirely closed;
    each of the plurality of PET detection modules comprises:
        a detector housing,
        a plurality of PET detection crystals arranged in a direction toward an interior of the PET detection cavity,
        a photosensor array, and
        a light guide,
        wherein the photosensor array, the light guide, and the plurality of PET detection crystals are disposed radially inwardly with respect to the common central axis; and
        wherein the light guide is coupled with both the photosensor array and the plurality of PET detection crystals;
    the cross-sectional areas of all gaps of the PET detection cavity are each smaller than a detection surface area of the smallest one of the PET detection crystals; the CT scanning frame further comprises the following devices: an X-ray tube, a filter, a collimator, a reference detector, and a detector;
    the PET detection cavity comprises a first operative configuration, a second operative configuration, a third operative configuration and a fourth operative configuration, wherein the PET detection cavity assumes one of the first operative configuration, the second operative configuration, the third operative configuration and the fourth operative configuration upon complete enclosure of the PET detection cavity, wherein an end of the PET detection cavity that is perpendicular to the common central axis has a first end cap allowing for entry and exit of an entire human body, wherein the first end cap comprises a mechanical structure that is openable and closable with respect to the PET detection cavity;
    in the first operative configuration, the PET detection cavity has a cylindrical shape and comprises a barrel in a middle of the cylindrical shape and two planar end caps at ends of the cylindrical shape respectively;
    in the second operative configuration, the PET detection cavity has a capsule shape and comprises a barrel in a middle of the capsule shape and two concave curved end caps at ends of the capsule shape respectively;
    in the third operative configuration, the PET detection cavity has an ellipsoidal shape with a>b=c; and the PET detection cavity comprises: two upper and lower hemi-ellipsoids or two left and right hemi-ellipsoids, or two left and right hemi-ellipsoids with a barrel sandwiched therebetween; and
    in the fourth operative configuration, the PET detection cavity has a regular polygonal prism shape and comprises a barrel in a middle of the regular polygonal prism shape and two planar end caps at ends of the regular polygonal prism shape respectively.

2. The whole-body PET and CT combined detector according to claim 1, wherein:
    in the first operative configuration, the barrel is composed of a plurality of detection module rings closely arranged to form a cylindrical shape, and each of the detection module rings is composed of a certain number of detection modules arranged circumferentially into a ring shape in a crystal-inward manner; the planar end cap is composed of a certain number of detection modules arranged in parallel into a disc shape or an approximate disc shape with detection surfaces of the crystals facing inward, and an inner side surface of the planar end cap formed into an approximately circular shape has a size larger than a circular opening of the barrel; the first end cap in the first form is one of the two planar end caps;
    in the second operative configuration, the barrel is composed of a plurality of detection module rings closely arranged to form a cylindrical shape, and each of the detection module rings is composed of a certain number of detection modules arranged circumferentially into a ring shape with detection surfaces of the crystals facing inward; the concave curved end cap is composed of a certain number of detection modules arranged in a certain curvature with detection surfaces of the crystals concave inward, and the cross section of the concave curved end cap perpendicular to an axis of the barrel is larger than a circular opening of the barrel having a capsule shape; the concave curved end cap is specifically one of the following three situations: a hemispherical end cap, a less-than-half ellipsoidal end cap or a less-than-half spherical crown-shaped end cap; the first end cap in the first form is one of the two concave curved end caps;
    in the third operative configuration, the upper and lower hemi-ellipsoids are mirror-symmetrical, and the left and right hemi-ellipsoids are mirror-symmetrical; the barrel is composed of a plurality of detection module rings closely arranged to form a cylindrical shape or a shape of truncated ellipsoid in the middle; each of the detection module rings in the barrel is composed of a certain number of detection modules arranged circumferentially into a ring shape with detection surfaces of the crystals facing inward; the first end cap in the third form is located on an end of the detection cavity perpendicular to the central axis; and
    in the fourth operative configuration, the barrel is composed of a plurality of detection module rings closely arranged to form a regular polygonal prism shape, and each of the detection module rings is composed of a certain number of detection modules arranged circumferentially into a regular polygon shape with detection surfaces of the crystals facing inward; the planar end cap having a regular polygonal prism shape is composed of a certain number of detection modules arranged in parallel into a disc shape or an approximate disc shape or a regular polygon shape or an approximately regular polygon shape with detection surfaces of the crystals facing inward; an inner side surface of the planar end cap having a regular polygonal prism shape formed into an approximately circular shape has a size larger than a regular polygon opening of the barrel having a regular polygonal prism shape; the first end cap in the fourth form is one of the two planar end caps having a regular polygonal prism shape.

3. The whole-body PET and CT combined detector according to claim 2, wherein:
a coincidence circuit is connected between every two PET detection modules;
a material of the PET detection crystals is a scintillation crystal, and the scintillation crystal is composed of one or more crystal blocks; and
in the fourth form, the regular polygonal prism is a regular hexagonal prism or a regular octagonal prism, and the regular polygon is a regular hexagon or a regular octagon.

4. The whole-body PET and CT combined detector according to claim 3, wherein:
the surfaces of the PET detection crystals that face inward are all planar or approximately planar;
the crystal block is specifically a crystal strip array composed of a plurality of crystal strips, or is composed of one or more integrally cut crystals;
a material of the scintillation crystal is selected from one or more of bismuth germanate (BGO) crystals, sodium iodide (NaI) crystals, NaI(Tl) single crystals, lutetium silicate (LSO) crystals, gadolinium silicate (GSO) crystals and yttrium lutetium silicate (LYSO);
spacers made of high atomic number substance are installed between all the detection module rings, or spacers made of high atomic number substance are installed between some of the detection module rings, or no spacers are installed between all the detection module rings; and
the high atomic number substance is lead or tungsten.

5. A whole-body PET and CT combined detector apparatus, comprising the whole-body PET and CT combined detector according to claim 1, wherein:
the whole-body PET and CT combined detector apparatus further comprises a power supply circuit, a communication line, a PC terminal, a PET bearing bracket, a CT bearing bracket, a scanning bed, a bed frame, an electric guide rail between the scanning bed and the bed frame, a PET working power source, a CT working power source, and a console terminal;
the PET bearing bracket fixes and supports all of the plurality of PET detection modules on the PET detection cavity, and the PET bearing bracket can drive the detection cavity to rotate at an arbitrary angle, and can also drive the detection cavity to translate in any direction;
the mechanical structure that can be opened and completely closed with respect to the PET detection cavity is a hinge structure that can be automatically or manually opened and closed in cooperation with the first end cap, or a rotation mechanism that enables the first end cap to be rotationally opened and closed while maintaining perpendicular to the central axis, or a translation mechanism that enables the first end cap to be opened and closed by translating while maintaining perpendicular to the central axis;
the PC terminal has a PET signal acquisition and operation analysis system, and a CT signal acquisition and operation analysis system;
the power supply circuit is connected to the PET working power source and the CT working power source; the PET working power source and the CT working power source provide electrical energy at a rated voltage to the communication line, the PC terminal, the PET bearing bracket, the CT bearing bracket, the scanning bed, the bed frame, the electric guide rail between the scanning bed and the bed frame, the console terminal and all the PET detection modules;
signals detected by all the PET detection modules are transmitted to the PET signal acquisition and operation analysis system through the communication line, and signals received by the detector and the reference detector in the CT scanning frame are transmitted to the CT signal acquisition and operation analysis system through the communication line;
the scanning bed is placed horizontally on the bed frame, a guide rail is provided between the scanning bed and the bed frame, and the scanning bed can move back and forth along the guide rail in a direction parallel to the central axis; and
a lower portion of the PET detection cavity has a gap through which one or more bed frames can pass.

6. The whole-body PET and CT combined detector apparatus according to claim 5, wherein:
a plurality of vertical pillars are provided under the bed frame along the central axis, and a horizontal, height-adjustable and stably supported pillar base is provided under each pillar; and
the guide rail is an integral rail, or is a pair of guide rails on both sides of the central axis.

7. A whole-body PET and CT combined detection method, which is implemented by using the whole-body PET and CT combined detector apparatus according to claim 6, wherein the method comprises:
1) a CT scanning step: placing an object to be detected onto the scanning bed, moving the scanning bed inwardly until a pre-scanning part is located in a middle position of the cylindrical CT scanning channel, and performing CT scanning detection to obtain a plurality of CT scanned static images;
2) a PET detecting step: for the case where the PET detection cavity is entirely closed, opening the first end cap, continuing to move the object to be detected inwardly under the driving of the scanning bed until the object to be detected completely enters the PET detection cavity, and completely closing the first end cap;
performing PET scanning detection on the object to be detected to obtain a plurality of PET scanned static images and at least one dynamic image; and
determining one or more parts of interest according to the plurality of PET scanned static images and the at least one dynamic image; and
3) a CT re-scanning step: selecting one re-scanning part from the one or more parts of interest, moving the scanning bed outward with the object to be detected carried thereon until the scanning part is located in the middle position of the cylindrical CT scanning channel, and then performing CT scanning detection again to obtain a plurality of CT scanned static images.

8. The whole-body PET and CT combined detection method according to claim 7, wherein:
the object to be detected is a human body detection module or a human body.

9. A whole-body PET and CT combined detection method, which is implemented by using the whole-body PET and CT combined detector apparatus according to claim 6, wherein the method comprises:
1) a PET detecting step: for the case where the PET detection cavity is entirely closed, opening the first end cap, continuing to move the object to be detected inwardly under the driving of the scanning bed until the object to be detected completely enters the PET detection cavity, and completely closing the first end cap;
performing PET scanning detection on the object to be detected to obtain a plurality of PET scanned static images and at least one dynamic image; and
determining one or more parts of interest according to the plurality of PET scanned static images and the at least one dynamic image; and
2) a CT scanning step: selecting one part of interest from the one or more parts of interest, moving the scanning bed outward with the object to be detected carried thereon until the part of interest is located in the middle position of the cylindrical CT scanning channel, and performing CT scanning detection to obtain a plurality of CT scanned static images.

\* \* \* \* \*